United States Patent
Jung et al.

(10) Patent No.: US 11,890,317 B2
(45) Date of Patent: *Feb. 6, 2024

(54) CELL-PROTECTING COMPOSITION CONTAINING CYCLO HISTIDINE-PROLINE AS ACTIVE INGREDIENT

(71) Applicant: NovMetaPharma Co., Ltd., Seoul (KR)

(72) Inventors: Hoe-Yune Jung, Pohang-si (KR); Heon-Jong Lee, Incheon (KR); Jong-Su Jeon, Pohang-si (KR); Yon-Su Kim, Seoul (KR); Seung-Hee Yang, Seoul (KR); Yong-Chul Kim, Seoul (KR); Jong-Joo Moon, Seoul (KR); Hwan-Soo Yoo, Cheongju-si (KR); Kyeong-Mi Choi, Cheongju-si (KR)

(73) Assignee: NovMetaPharma Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/856,729

(22) Filed: Jul. 1, 2022

(65) Prior Publication Data

US 2022/0331396 A1 Oct. 20, 2022

Related U.S. Application Data

(60) Continuation-in-part of application No. 17/172,879, filed on Feb. 10, 2021, now Pat. No. 11,433,114, which is a division of application No. 16/316,595, filed as application No. PCT/KR2017/007518 on Jul. 13, 2017, now Pat. No. 10,918,693.

(30) Foreign Application Priority Data

Jul. 13, 2016 (KR) .................. 10-2016-0088751
Jul. 12, 2017 (KR) .................. 10-2017-0088341

(51) Int. Cl.
| | | |
|---|---|---|
| *A61K 38/05* | (2006.01) | |
| *A61K 38/12* | (2006.01) | |
| *A23L 33/18* | (2016.01) | |
| *A61P 31/00* | (2006.01) | |
| *A61P 35/00* | (2006.01) | |
| *C07K 5/12* | (2006.01) | |
| *A23L 33/00* | (2016.01) | |
| *A61P 1/16* | (2006.01) | |

(52) U.S. Cl.
CPC .............. *A61K 38/12* (2013.01); *A23L 33/00* (2016.08); *A23L 33/18* (2016.08); *A61K 38/05* (2013.01); *A61P 31/00* (2018.01); *A61P 35/00* (2018.01); *C07K 5/12* (2013.01); *A23V 2002/00* (2013.01); *A23V 2200/308* (2013.01); *A23V 2250/55* (2013.01); *A61P 1/16* (2018.01)

(58) Field of Classification Search
CPC .......... A61K 38/05; A61K 38/12; C07K 5/06; C07K 5/12
See application file for complete search history.

(56) References Cited

U.S. PATENT DOCUMENTS

| | | | |
|---|---|---|---|
| 6,060,446 A | 5/2000 | Zaloga et al. | |
| 10,792,280 B2 | 10/2020 | Kim et al. | |
| 10,918,693 B2 | 2/2021 | Jung et al. | |
| 11,433,114 B2 * | 9/2022 | Jung | ...................... A23L 33/18 |
| 2010/0048887 A1 | 2/2010 | Anderson et al. | |
| 2010/0183520 A1 | 7/2010 | Ramesh | |
| 2013/0303463 A1 | 11/2013 | Bar-Or | |
| 2014/0113884 A1 | 4/2014 | Imig et al. | |
| 2015/0051223 A1 | 2/2015 | Bar-Or et al. | |
| 2018/0186897 A1 * | 7/2018 | Lanzavecchia | .. C07K 14/70503 |
| 2018/0312606 A1 * | 11/2018 | Zhou | ...................... A61P 35/00 |

OTHER PUBLICATIONS

Alba Minelli et al. "Cyclo(His-Pro) exerts anti-inflammatory effects by modulating NF-B and Nrf2 signalling", The International Journal of Biochemistry & Cell Biology, vol. 44, 2012, pp. 525-535 (11 pages total).
Alba Minelli et al. "Phosphoproteomic analysis of the effect of cyclo-[His-Pro] dipeptide on PC12 cells" Peptides, vol. 27, 2006, pp. 105-113 (9 pages total).
Koo, Kwang Bon et al., "Protective Effect of Cydo(His-Pro) on Streptozotocin-Induced Cytotoxicity and Apoptosis In Vitro," J. Microbiol. Biotechnol, vol. 21, No. 2 pp. 218-227, 2011.
Song, Moon K. et al., "Anti-Hyperglycemic Activity of Zinc Plus Cycle (His-Pro) in Genetically Diabetic Goto-Kakizaki and Aged Rats," Exp Biol Med, vol. 228, pp. 1338-1345, 2003.
Song, Moon K. et al., "Raw vegetable food containing high cyclo (his-pro) improved insulin sensitivity and body weight xantrol," Metabolism, vol. 54, pp. 1480-1489, 2005.
Brauns et al. Selected Cyclic Dipeptides Inhibit Cancer Cell Growth and Induce Apoptosis in HT-29 Colon Cancer Cells. Anticancer Research. 2004, vol. 24, pp. 1713-1720. (Year: 2004).
Cornacchia et al.. 2,5-Diketopiperazines as Neuroprotective Agents, Mini-Reviews in Medicinal Chemistry. 2012, vol. 12, No. 1, p. 2-12. (Year: 2012).
Minelli et al. Focus on cyclo(His-Pro): history and perspectives as antioxidant peptide. Amino acids. 2008, vol. 35, pp. 283-289. (Year: 2008).
Ong et al. Synergistic Antidiabetic Activities of Zinc, Cyclo (His-Pro), and Arachadonic Acid. Metabolism. Jan. 2001, vol. 50, No. 1, pp. 53-59. (Year: 2001).
Bellezzaa et al., "Neuroinflammation and endoplasmic reticulum stress arecoregulated by cyclo(His-Pro) to prevent LPS neurotoxicity", The International Journal of Biochemistry & Cell Biology, vol. 51, 2014, pp. 159-169, (11 pages total).

(Continued)

*Primary Examiner* — Jeffrey E. Russel
(74) *Attorney, Agent, or Firm* — Sughrue Mion, PLLC (57) ABSTRACT

A new use of a cyclo histidine-proline (Cyclo His-Pro, CHP) is disclosed. A composition including cyclo histidine-proline (CHP) as an active ingredient has an excellent protective effect to protect kidney and liver cells from damage and/or toxicity induced by various causes. The composition is useful and effective in protecting kidney and/or liver cells/tissues and in treating a subject with kidney and/or liver diseases and/or damages.

14 Claims, 8 Drawing Sheets

(56) References Cited

OTHER PUBLICATIONS

Minelli et al., "Cyclo(His-Pro) promotes cytoprotection by activating Nrf2-mediated up-regulation of antioxidant defense", J. Cell. Mol. Med., vol. 13, No. 6, 2009, pp. 1149-1161, (13 pages total).
Takahashi et al., Folia Pharmacologica Japonica 130(4), pp. 252-256, Oct. 1, 2007, with English Abstract.
European Office Action dated Feb. 7, 2023, issued in European Application No. 20206943.1.
Limdi J K et al., "Evaluation of abnormal liver function tests", Postgraduate Medical Journal, vol. 79, No. 932, 2003, pp. 307-312 (6 pages total).

\* cited by examiner

CELL-PROTECTING COMPOSITION CONTAINING CYCLO HISTIDINE-PROLINE AS ACTIVE INGREDIENT

CROSS REFERENCE TO RELATED APPLICATIONS

This application is Continuation-in-part Application of U.S. application Ser. No. 17/172,879 filed Feb. 10, 2021 now U.S. Pat. No. 11,433,114 which is a Divisional Application of U.S. application Ser. No. 16/316,595, filed on Jan. 9, 2019 (now U.S. Pat. No. 10,918,693), which is a National Stage Application of International Application No. PCT/KR2017/007518, filed on Jul. 13, 2017, which claims priority from Korean Patent Application No. 10-2016-0088751 filed on Jul. 13, 2016 and Korean Patent Application No. 10-2017-0088341 filed on Jul. 12, 2017, in the Korean Intellectual Property Office, of which the contents are incorporated herein by reference in their entireties.

TECHNICAL FIELD

The present disclosure relates to a composition for cell protection that includes cyclo histidine-proline (Cyclo His-Pro, CHP) as an active ingredient.

BACKGROUND ART

Cyclo histidine-proline (Cyclo His-Pro, CHP) is a naturally-generating cyclic dipeptide that is structurally related to thyrotropin-releasing hormone (TRH). The cyclo histidine-proline (CHP) is a peptide inherent in animal and human tissues and body fluids. The CHP is found in blood, semen, gastrointestinal tract, urine, etc., and in particular is a metabolite rich in prostate. The cyclo histidine-proline (CHP) has been known to have a variety of physiological functions such as anti-diabetes, anti-obesity, anti-inflammatory and antioxidant effects.

Apoptosis is an important process in the normal development and function of multicellular organisms. Physiological apoptosis plays an important role in normal processes, but abnormal apoptosis causes various diseases. For example, inhibition of apoptosis may lead to cancer, autoimmune diseases, inflammatory diseases, and viral infections.

Further, the apoptosis is known to be associated with degenerative neurological diseases such as Alzheimer's disease, Parkinson's disease, amyotrophic lateral sclerosis, and Lou Gehrig's disease, and acute diseases such as cerebral ischemia, traumatic brain injury, spinal cord injury, and stroke.

However, there has been no report on the cytoprotective effect of the cyclo histidine-proline (CHP) and its mechanism.

DISCLOSURE

Technical Problem

The present inventors have experimentally confirmed that the cyclohistidine-proline (CHP) inhibits apoptosis of kidney cells and liver cells induced by high-level drug treatment and protects cells, thereby to complete the present disclosure.

One purpose of the present disclosure is to provide a cell-protecting pharmaceutical composition including the cyclo histidine-proline (CHP) or a pharmaceutically acceptable salt thereof as an active ingredient.

Another purpose of the present disclosure is to provide a health functional food for preventing or ameliorating liver or kidney damage, the food including the cyclo histidine-proline (CHP) or a food acceptable salt thereof as an active ingredient.

Technical Solution

To this end, the present disclosure provides a cell-protecting pharmaceutical composition including the cyclo histidine-proline (CHP) or a pharmaceutically acceptable salt thereof as an active ingredient.

According to an embodiment of the present disclosure, the cell may be a kidney cell or a liver cell.

According to an embodiment of the present disclosure, the composition may inhibit apoptosis.

According to an embodiment of the present disclosure, the composition may inhibit drug-induced cellular damage.

According to an embodiment of the present disclosure, the drug may be an anticancer agent or an antibiotic agent, in which the anticancer agent may be one or more platinum-based anticancer agents selected from a group consisting of cisplatin, carboplatin, oxaliplatin and nedaplatin.

Further, the present disclosure provides a health functional food for preventing or ameliorating liver or kidney damage, the food including the cyclo histidine-proline (CHP) or a food acceptable salt thereof as an active ingredient.

According to an embodiment of the present disclosure, a drug inducing the liver or kidney toxicity or damage may be one or more anticancer agents or antibiotic agents selected from a group consisting of cisplatin, gentamycin (GM) and acetaminophen (APAP).

Advantageous Effects

According to the present disclosure, the cell-protecting pharmaceutical composition including the cyclo histidine-proline (Cyclo His-Pro, CHP) as an active ingredient may inhibit the apoptosis of kidney cells or liver cells caused by toxicity. Thus, the composition may be useful as a composition for preventing and treating kidney and liver toxicity.

BEST MODES

The present disclosure is described in detail below.

The cell-protecting composition including the cyclo histidine-proline (Cyclo His-Pro, CHP) as an active ingredient according to the present disclosure has been confirmed to inhibit the apoptosis of kidney or liver cells.

The present disclosure provides a cell-protecting composition including the cyclo histidine-proline (CHP) or a pharmaceutically acceptable salt thereof as an active ingredient. According to an embodiment of the present disclosure, the cyclo histidine-proline (CHP) may be isolated from prostate extract.

[Chemical formula 1]

The cell-protecting composition including the cyclo histidine-proline (CHP) or a pharmaceutically acceptable salt thereof as an active ingredient according to the present disclosure may protect kidney cells or liver cells.

The composition including the cyclo-histidine-proline (CHP) as an active ingredient according to the present disclosure may inhibit apoptosis.

The composition according to the present disclosure is to inhibit drug-induced cell damage. The drug may be an anticancer agent or an antibiotic agent. Specifically, the drug may be one or more platinum-based anticancer agents selected from a group consisting of cisplatin, carboplatin, oxaliplatin and nedaplatin; or an antibiotic agent such as gentamycin or acetaminophen.

The pharmaceutical composition according to the present disclosure may further include suitable carriers, excipients or diluents conventionally used in the manufacture of pharmaceutical compositions. In this connection, a content of the cyclo histidine-proline (CHP), salt, extract or fraction thereof included in the composition may be preferably 0.0001 to 10% by weight, preferably 0.001 to 1% by weight. However, the present disclosure is not particularly limited thereto. As used herein, the term "pharmaceutically acceptable salt" refers to a salt that can be pharmaceutically used, among the substances having cations and anions coupled by electrostatic attraction. Typically, it may include metal salts, salts with organic bases, salts with inorganic acids, salts with organic acids, salts with basic or acidic amino acids or the like. Examples of the metal salts may include alkali metal salts (sodium salts, potassium salts, etc.), alkaline earth metal salts (calcium salts, magnesium salts, barium salts, etc.), aluminum salts or the like; examples of the salts with organic bases may include salts with triethylamine, pyridine, picoline, 2,6-lutidine, ethanolamine, diethanolamine, triethanolamine, cyclohexylamine, dicyclohexylamine, N,N'-dibenzylethylenediamine or the like; examples of the salts with inorganic acids may include salts with hydrochloric acid, hydrobromic acid, nitric acid, sulfuric acid, phosphoric acid, or the like; examples of the salts with organic acids may include salts with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid or the like; examples of the salts with basic amino acids may include salts with arginine, lysine, omithine or the like; and examples of the salt with acidic amino acids include salts with aspartic acid, glutamic acid or the like.

The composition according to the present disclosure is preferably a pharmaceutical composition. The pharmaceutical composition may be administered orally or parenterally. Extracorporeal or intraperitoneal injection, intrarectal injection, subcutaneous injection, intravenous injection, intramuscular injection or intrathoracic injection may be preferably selected for parenteral administration.

The pharmaceutical composition according to the present disclosure may further include commonly used excipients, disintegrants, sweeteners, lubricants, flavors, and the like. The disintegrant may be selected from the group consisting of sodium starch glycolate, crospovidone, croscarmellose sodium, alginic acid, carboxymethylcellulose calcium, carboxymethylcellulose sodium, chitosan, guar gum, low-substituted hydroxypropylcellulose, magnesium aluminum silicate, and polacrilin potassium. Further, the pharmaceutical composition according to the present disclosure may further include a pharmaceutically acceptable additive. In this connection, the pharmaceutically acceptable additives may include starch, gelatinized starch, microcrystalline cellulose, lactose, povidone, colloidal silicon dioxide, calcium hydrogen phosphate, lactose, mannitol, sugar, arabic gum, pregelatinized starch, corn starch, powdered cellulose, hydroxypropylcellulose, opadry, sodium starch glycolate, carnauba lead, synthetic aluminum silicate, stearic acid, magnesium stearate, aluminum stearate, calcium stearate, white sugar, dextrose, sorbitol, talc, etc. The content of one or more pharmaceutically acceptable additive(s) according to the present disclosure may be in a range of 0.1 to 90 parts by weight based on the total weight of the pharmaceutical composition.

Solid form preparations for oral administration include powders, granules, tablets, capsules, soft capsules, pills and the like. Liquid preparations for oral administration include suspensions, solutions, emulsions, syrups, aerosols and the like. The liquid preparation may include various excipients such as a wetting agent, a sweetening agent, a fragrance, and a preservative in addition to water and liquid paraffin which are commonly used simple diluents. Formulations for parenteral administration may be formulated in the form of external preparations such as powders, granules, tablets, capsules, sterilized aqueous solutions, liquid preparations, non-aqueous solvents, suspensions, emulsions, syrups, suppositories, and aerosols and sterile injectable preparation, respectively, according to conventional methods. Preferably, externally-applied skin pharmaceutical preparations such as creams, gels, patches, sprays, ointments, alerts, lotions, liniments, pastes or cataplasms may be prepared, but are not limited thereto. As the non-aqueous formulation or suspension, propylene glycol, polyethylene glycol, vegetable oil such as olive oil, injectable ester such as ethyl oleate, or the like may be used. witepsol, macrogol, tween 61, cocoa butter, laurin butter, glycerogelatin or the like may be used as a base of the suppository.

The preferred dosage of the pharmaceutical composition according to the present disclosure varies depending on the degree of absorption of the active substance in the body, inactivation and excretion rate, age, sex and condition of the patient, and severity of the disease to be treated. The dosage may be suitably selected by those skilled in the art. However, for the desired effect, in the case of oral administration, generally, the pharmaceutical composition according to the present disclosure may be administered to one adult at a dosage of 0.0001 to 100 mg/kg, preferably 0.001 to 100 mg/kg per a day. The administration may be carried out once a day or divided into several times for one day. The dosage does not in any respect limit the scope of the present disclosure. The pharmaceutical composition according to the present disclosure has little toxicity and side effects, and may be used safely even when taken for a long time.

Because the pharmaceutical composition according to the present disclosure has an excellent effect of protecting kidney cells, the composition may prevent or treat diseases including, but not limited to nephritis, acute pyelonephritis, chronic pyelonephritis, acute renal failure, renal tubulo-interstitial fibrosis disorder, nephrotic syndrome, nephrogenic diabetes insipidus, electrolyte metabolism abnormality hyperuricemia, hyponatremia, etc. Because the pharmaceutical composition according to the present disclosure has an excellent effect of protecting liver cells, the pharmaceutical composition according to the present disclosure may be useful for the prevention or treatment of diseases selected from the group consisting of hepatic failure, acute hepatitis, chronic hepatitis, liver cirrhosis, hepatic coma and alcoholic liver disease.

The composition according to the present disclosure including the cyclo histidine-proline (Cyclo His-Pro, CHP) or its pharmaceutically acceptable salt as an active ingredient may be used as an anticancer adjuvant for the prevention or treatment of liver or kidney toxicity as induced by an anticancer drug.

The anticancer adjuvant may be administered in combination with an existing anticancer drug such as cisplatin, carboplatin, oxaliplatin, nedaplatin, doxorubicin, taxol, tamoxifen, camptobel, adlucil, gleevec, etoposide, zometa, and oncovin to reduce liver or kidney toxicity to improve anticancer efficacy.

Further, the present disclosure provides a health functional food for preventing or ameliorating liver or kidney damage, the food including as an active ingredient the cyclo histidine-proline (Cyclo His-Pro, CHP) or a food acceptable salt thereof.

The drug that induces liver or kidney damage may be one or more anticancer agents or antibiotic agents selected from a group consisting of cisplatin, gentamycin (GM), and acetaminophen (APAP).

As used herein, the term "food acceptable salt" refers to a salt that can be used as food, among the substances having cations and anions coupled by electrostatic attraction. Specific examples of the food acceptable salt include examples of the above-mentioned pharmaceutically acceptable salts.

As used herein, the term "health food" refers to foods that have an active health maintaining or promoting effect compared to general foods. The term "health supplement food" means foods for health supplementing. In some cases, the functional foods, health foods, and health supplements may be used in an interchangeable manner. The food may be prepared in various forms such as tablets, capsules, powders, granules, liquids, and pills in order to obtain useful effects.

As used herein, the term "functional food" is the same term as "food for special health use (FoSHU)". This food means foods with high medical effects that have been processed so that the biocontrol function can be efficiently enabled in addition to nutrition.

As a specific example of such a health functional food, a processed food may be produced having good storage properties while converting the above-mentioned composition into foods having characteristics of agricultural products, livestock products or aquatic products.

Because the health functional food according to the present disclosure has an excellent effect of protecting kidney cells, the food may prevent or treat diseases selected from the group consisting of nephritis, acute pyelonephritis, chronic pyelonephritis, acute renal failure, renal tubulo-interstitial fibrosis disorder, nephrotic syndrome, nephrogenic diabetes insipidus, electrolyte metabolism abnormality hyperuricemia, hyponatremia, etc. Further, because the health functional food according to the present disclosure has an excellent effect of protecting liver cells, the food may prevent or treat diseases selected from the group consisting of hepatic failure, acute hepatitis, chronic hepatitis, liver cirrhosis, hepatic coma and alcoholic liver disease.

EXEMPLARY EMBODIMENTS

Example 1

Analysis of Kidney Apoptosis Inhibition by Cyclo Histidine-Proline (CHP)

We confirmed that the cyclo histidine-proline (CHP) inhibited the apoptosis of kidney cells as induced by gentamicin (GM).

Figure 1A:
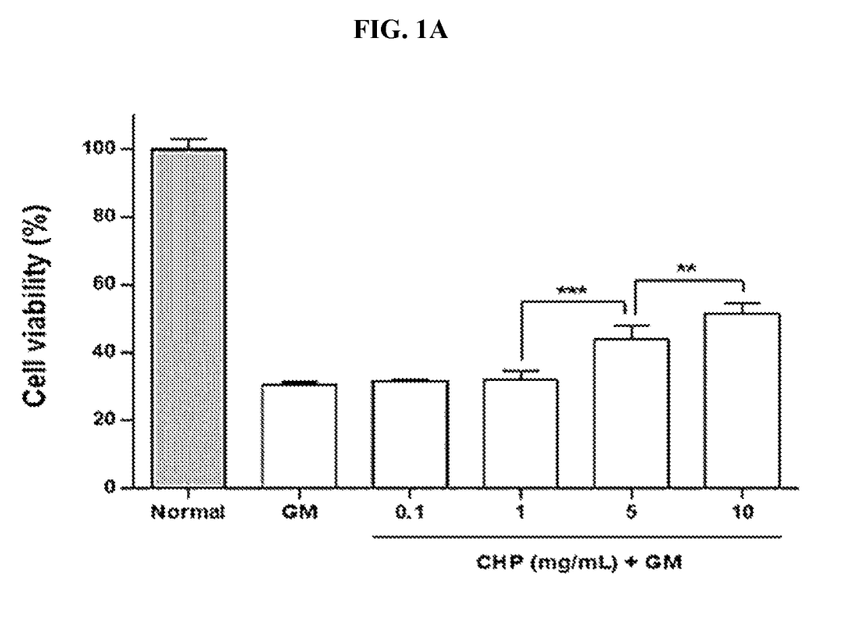
FIG. 1A and FIG. 1B illustrate an apoptosis inhibition effect for GM inducing kidney cells (LLC-PK1 cells) by CHP:  $P<0.01$, * $P<0.001$. CHP; Cyclo His-Pro, GM; gentamicin.

Specifically, the cyclo histidine-proline (CHP) was produced by requesting only a target spec (99% purity) from a peptide manufacturer (Bachem; Bubendorf, Switzerland). The gentamycin was purchased from Sigma Chemical Co. (St. Louis, Mo., USA). The kidney cells (LLC-PK1 cells) were purchased from the American Type Culture Collection (ATCC; Manassas, VA, USA). The present inventors simultaneously treated and cultured the kidney cell (LLC-PK1 cell) with CHP 0.1, 1, 5 or 10 mg/mL respectively together with GM 5 mg/mL for 6 hours (FIG. 1A).

Figure 1B:
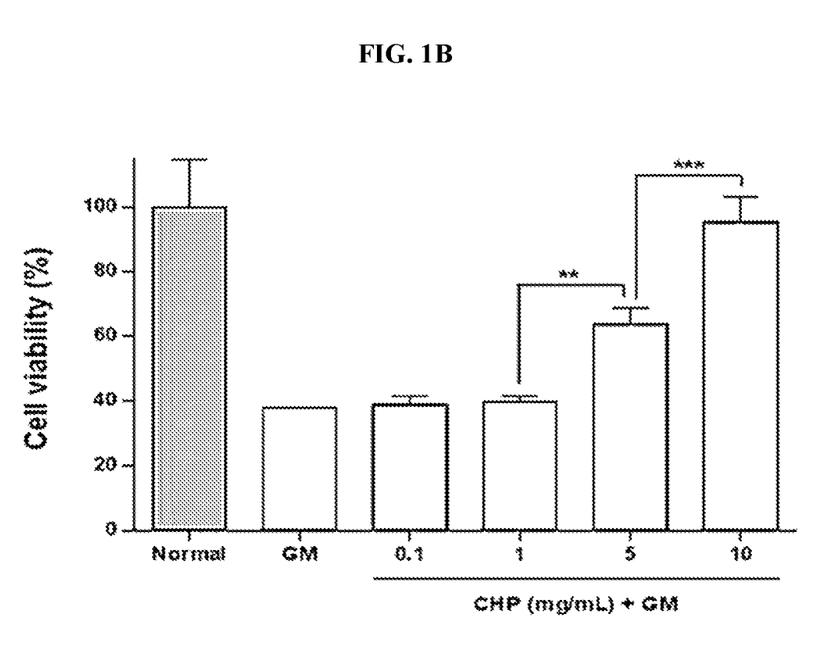

Further, the present inventors pre-treated and pre-cultured the kidney cell (LLC-PK1 cell) with CHP 0.1, 1, 5 or 10 mg/mL for 2 hours and subsequently post-treated and post-cultured the kidney cell (LLC-PK1 cell) with GM 5 mg/mL for 4 hours (FIG. 1B). The cell viability was analyzed using cell counting kit-8 (Dojindo Laboratories; Kumamoto, Japan). Subsequently, the cell viability was measured with a microplate reader (Molecular Devices, LLC; Sunnyvale, CA, USA).

As a result, the gentamycin (GM) induced apoptosis of kidney cells. The cyclo histidine-proline (CHP) inhibited the apoptosis of kidney cells induced by the gentamicin (GM) in a concentration-dependent manner. In particular, when the kidney cells were pre-treated with the above cyclo histidine-proline (CHP), the gentamicin (GM)-induced apoptosis was greatly inhibited.

Example 2

Analysis of Liver Apoptosis Inhibition by Cyclo Histidine-Proline (CHP)

We confirmed that the cyclo histidine-proline (CHP) inhibited the apoptosis of liver cells as induced by acetaminophen (APAP).

Figure 2A:
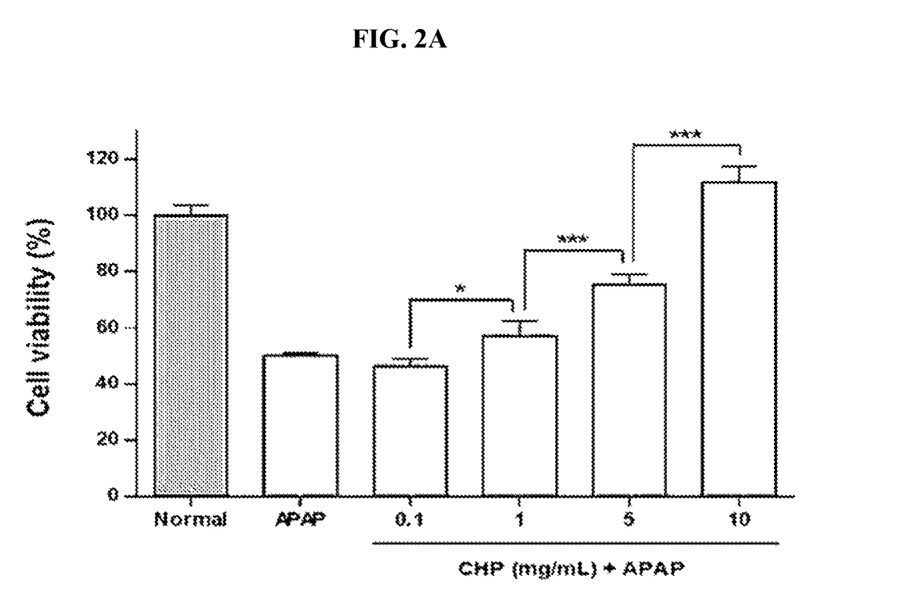
FIG. 2A and FIG. 2B illustrate an apoptosis inhibition effect for APAP inducing liver cell (Chang liver cell) by CHP: * $P<0.05$, *** $P<0.001$. CHP; Cyclo His-Pro, APAP; acetaminophen.

Specifically, the acetaminophen was purchased from Sigma Chemical Co. (St. Louis, Mo., USA). The liver cells (Chang liver cells) were purchased from the American Type Culture Collection (ATCC; Manassas, VA, USA). The present inventors simultaneously treated and cultured the liver cell (Chang liver cell) with CHP 0.1, 1, 5 or 10 mg/mL respectively together with APAP 15 mM for 24 hours (FIG. 2A).

Figure 2B:
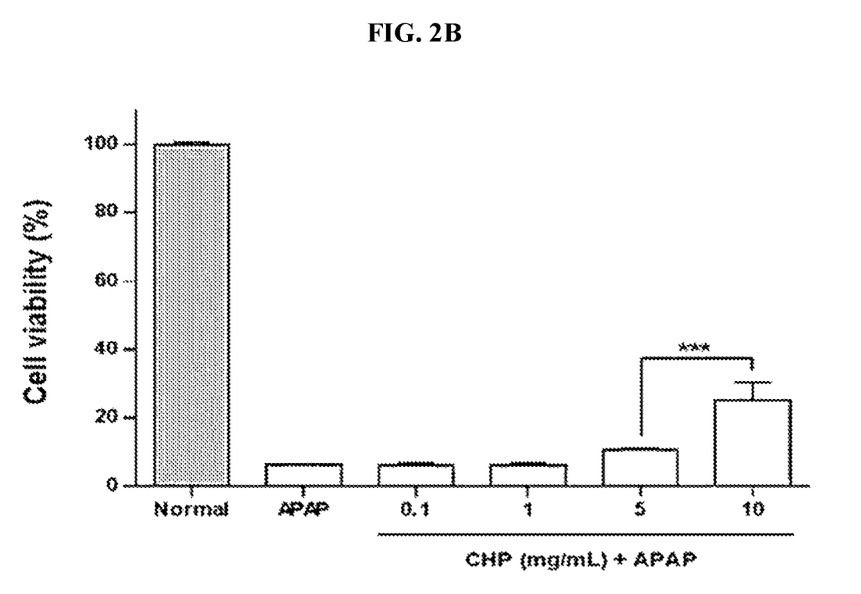

Further, the present inventors pre-treated and pre-cultured the liver cell (Chang liver cell) with CHP 0.1, 1, 5 or 10 mg/mL for 24 hours and subsequently post-treated and post-cultured the liver cell (Chang liver cell) with APAP 15 mM for 24 hours (FIG. 2B). The cell viability was analyzed using cell counting kit-8 (Dojindo Laboratories; Kumamoto, Japan). Subsequently, the cell viability was measured with a microplate reader (Molecular Devices, LLC; Sunnyvale, CA, USA).

As a result, the acetaminophen (APAP) induced apoptosis of liver cells. The cyclo histidine-proline (CHP) inhibited the apoptosis of liver cells induced by the acetaminophen (APAP) in a concentration-dependent manner.

In particular, the acetaminophen (APAP)-induced apoptosis was significantly inhibited when the liver cells were co-treated with the acetaminophen (APAP) and the cyclo histidine-proline (CHP).

Example 3

Analysis of Inhibition of Liver Damage by Cisplatin in an Animal Model by Ingestion of Cyclo Histidine-Proline (CHP)

<3-1> CHP Ingestion and Administration of Cisplatin

To determine the protective effect of CHP on liver toxicity in mice, the present inventors purchased SD mice from Koatech, and the mice were raised under constant conditions (temperature: 23±3° C., relative humidity: 55±10%, daily cycle: 12 hours). Five mice were grouped into one group. We fed water and food to mice in the cage. We adapted the mice for experiments for one week prior to the experiment. After the adaption period, the mice were grouped into five groups. We conducted the experiment as shown in Table 1 below.

TABLE 1

| GROUP | CHP (mg/L) | Cisplatin (mg/kg) | Period |
|---|---|---|---|
| 1. Normal control | — | — | For 1 week, the mice ingested CHP in drinking water at each concentration and we administered the mice with cisplatin 7.5 mg/kg by intraperitoneal injection. |
| 2. Cisplatin control | — | 7.5 | |
| 3. CHP ingestion group | 1 | | |
| 4. CHP ingestion group | 5 | | |
| 5. CHP ingestion group | 10 | | |

1 group ingested water and was set as a negative control. 2 group ingested water, and was subjected to cisplatin treatment, and was set as a liver damage control. 3 group ingested 1 mg/L of CHP in drinking water and, after one week, was subjected to cisplatin treatment. 4 group ingested 5 mg/L of CHP in drinking water and, after one week, was subjected to cisplatin treatment. 5 group ingested 10 mg/L of CHP in drinking water and, after one week, was subjected to cisplatin treatment. These 3, 4 and 5 groups were set as liver damage prevention effect groups. The CHP ingestion using drinking water was performed once every two days.

<3-2> Measurement of Liver Function Protection Effect of Mouse

To confirm the liver function protection effect by CHP, we firstly administered CHP to mice for one week at each concentration, followed by cisplatin treatment, and, then, after 24 hours, mouse liver function was confirmed. To measure ALT and AST, we collected blood from the abdominal aorta from a mouse. We separated only serum from the blood using a centrifugal separator and analyzed the serum using an automatic analyzer (Hitachi 7180; Tokyo, Japan).

Figure 3:
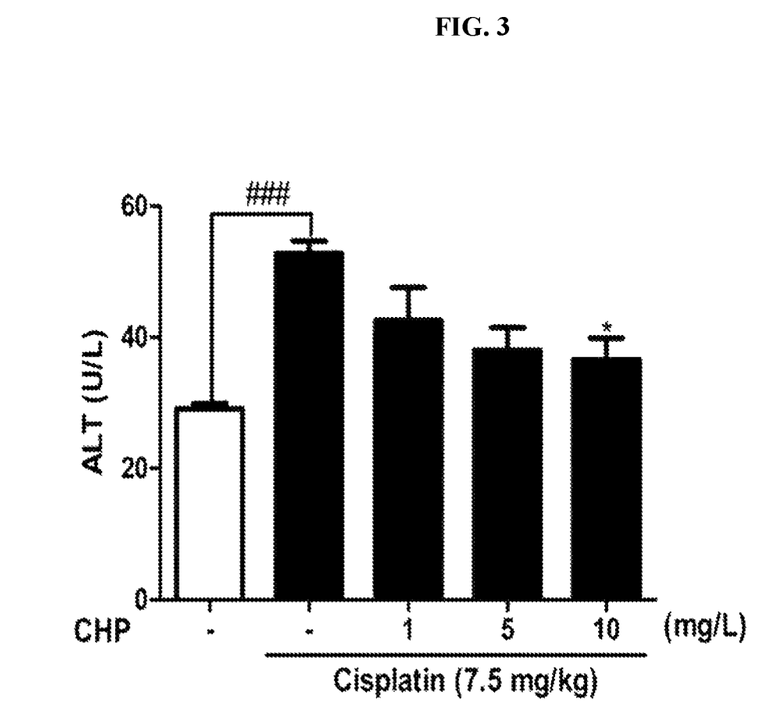
FIG. 3 is a graph of an ALT measurement to confirm that CHP ingestion protects a mouse against liver toxicity by cisplatin.
Figure 4:
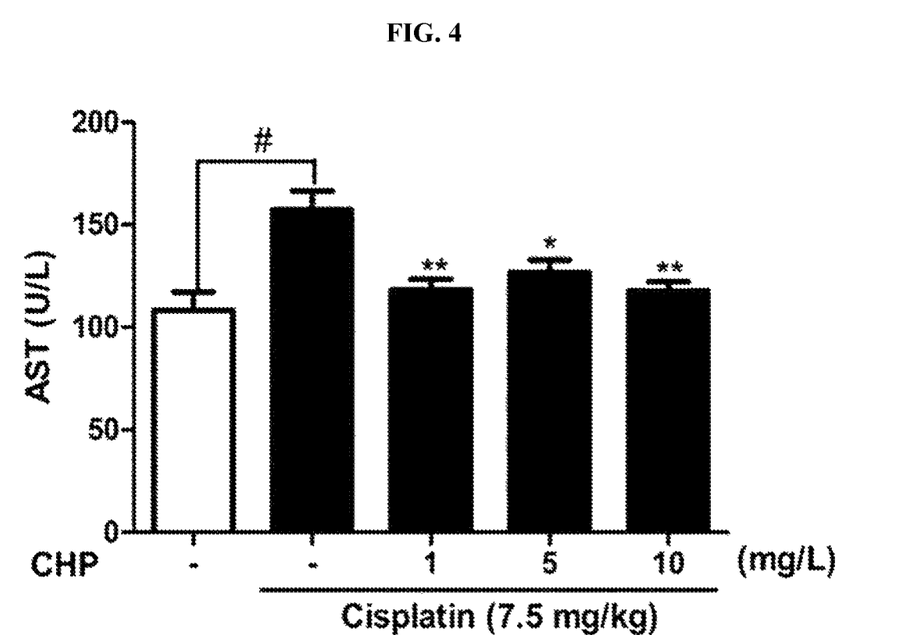
FIG. 4 is a graph of an AST measurement to confirm that CHP ingestion protects a mouse against liver toxicity by cisplatin.

As a result, as illustrated in FIGS. 3 and 4, we conducted a t-verification on the negative control and the liver damage group induced by cisplatin and verified significance thereof. The two group showed statistically significant differences (* $p<0.05$, *** $p<0.0005$).

Further, multiple comparisons were made between the cisplatin-induced liver damage group and CHP ingestion groups with significant differences ANOVA. We conducted individual comparisons using the Turkish post-test thereon. Those groups showed statistically significant differences (* $p<0.05$, ** $p<0.005$).

The administration of cisplatin in mice could also lead to liver damage and increased ALT and AST. Further, it was confirmed that in mice injected with CHP, cisplatin-induced ALT and AST were significantly reduced.

Therefore, CHP exhibits excellent effects of reducing ALT and AST concentrations that enable blood liver function values to be confirmed. Thus, the pharmaceutical composition including the CHP as an active ingredient is excellent in protecting liver cells. Thus, it may be known that the CHP may be useful for preventing or treating diseases caused by liver disease.

Example 4

Analysis of Inhibition of Kidney Damage by Cisplatin in an Animal Model by Ingestion of Cyclo Histidine-Proline (CHP)

<4-1> CHP Ingestion and Administration of Cisplatin

To determine the protective effect of CHP on kidney toxicity in mice, the present inventors purchased ICR mice from Koatech, and the mice were raised under constant conditions (temperature: 23±3° C., relative humidity: 55±10%, daily cycle: 12 hours). Five mice were grouped into one group. We fed water and food to mice in the cage. We adapted the mice for experiments for one week prior to the experiment. After the adaption period, the mice were grouped into 3 groups. We conducted the experiment as shown in Table 2 below.

TABLE 2

| Group | CHP (mg/kg) | Cisplatin (mg/kg) | Period |
|---|---|---|---|
| 1. Normal control | — | — | For 1 week, the mice ingested CHP orally daily and we administered the mice with cisplatin 10 mg/kg by intraperitoneal injection. |
| 2. Cisplatin control | — | 10 | |
| 3. CHP ingestion group | 1 | | |

1 group ingested water orally and was set as a negative control. 2 group ingested orally water, and was subjected to cisplatin treatment, and was set as a kidney damage control. 3 group ingested CHP orally daily for one week at a 1 mg/kg concentration, and then was subjected to cisplatin treatment. The 3 group was set as a kidney damage prevention effect group.

<4-2> Measurement of Kidney Function Protection Effect of Mouse

Figure 5:
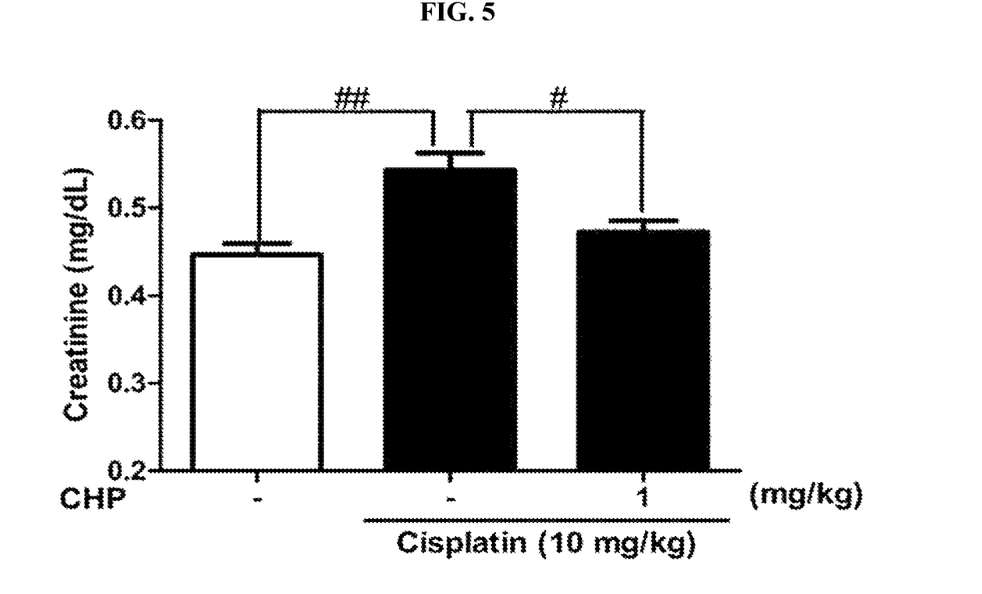
FIG. 5 is a graph of a creatinine measurement to confirm that CHP ingestion protects a mouse against kidney toxicity by cisplatin.

To confirm the kidney function protection effect by CHP, first, we orally administered the cyclo histidine-proline (CHP) via syringe at a dose of 1 ml per day to the mice at a concentration of 1 mg/kg for one week, followed by the cisplatin treatment. Then, after 72 hours, the kidney function of the mice was checked. To measure creatinine, we collected a blood from the mouse heart and we separated serum only from the blood using a centrifugal separator. We analyzed the serum using a biochemical analysis equipment (BS-390, Mindray Bio-Medical Electronics Co., Ltd., China). The results of the analysis are illustrated in FIG. 5. We performed a t-verification between the liver damage group treated with cisplatin and other experimental groups and verified the significance thereof. These groups showed a statistically significant difference (*p<0.05, ** p<0.005).

As illustrated in FIG. 5, the administration of cisplatin to mice could also lead to kidney damage and increase in creatinine. Further, it was confirmed that the cisplatin-induced creatinine was significantly reduced in mice that ingested the cyclo histidine-proline (CHP).

Thus, the cyclo histidine-proline (CHP) has the effect of reducing the concentration of creatinine, which allows the kidney function value in blood to be measured. Therefore, the pharmaceutical composition including the cyclo histidine-proline (CHP) as the active ingredient is excellent in protecting the kidney cell. Thus, it is also known that such a composition may be usefully used for the prevention or treatment of diseases including the kidney disease.

Example 5

Measurement of Inhibition Effect of Kidney Damage Induced by Cisplatin in Mice Via Ingestion of Cyclo Histidine-Proline (CHP)

<5-1> Cyclo Histidine-Proline (CHP) Ingestion and Cisplatin Administration

To determine the protective effect of CHP on kidney toxicity in mice, the present inventors purchased ICR mice from Koatech, and the mice were raised under constant conditions (temperature: 23±3° C., relative humidity: 55±10%, daily cycle: 12 hours). Five mice were grouped into one group. We fed water and food to mice in the cage. We adapted the mice for experiments for one week prior to the experiment. After the adaption period, the mice were grouped into 3 groups. We conducted the experiment as shown in Table 3 below.

TABLE 3

| Group | CHP (mg/kg) | Cisplatin (mg/kg) | Period |
|---|---|---|---|
| 1. Normal control | — | — | For 1 week, the mice ingested CHP orally daily and we administered the mice with cisplatin 10 mg/kg by intraperitoneal injection. |
| 2. Cisplatin control | — | 30 | |
| 3. CHP ingestion group | 1 | | |

1 group ingested water orally and was set as a negative control. 2 group ingested orally water, and was subjected to cisplatin treatment, and was set as a kidney damage control. 3 group ingested CHP orally daily for one week at a concentration 1 mg/kg, and, was subjected to cisplatin treatment. The 3 group was set as a kidney damage prevention effect group.

<5-2> Measurement of Kidney Function Protection Effect of Mouse

To confirm the kidney function protection effect by CHP, first, we orally administered the cyclo histidine-proline (CHP) to the mice at a concentration of 1 mg/kg daily for one week, followed by the cisplatin treatment. Then, after 24 hours, the kidney function of the mice was checked. To measure BUN, we collected a blood from the mouse heart and we separated serum only from the blood using a centrifugal separator. We analyzed the serum using a biochemical analysis equipment (BS-390, Mindray Bio-Medical Electronics Co., Ltd., China).

Figure 6:
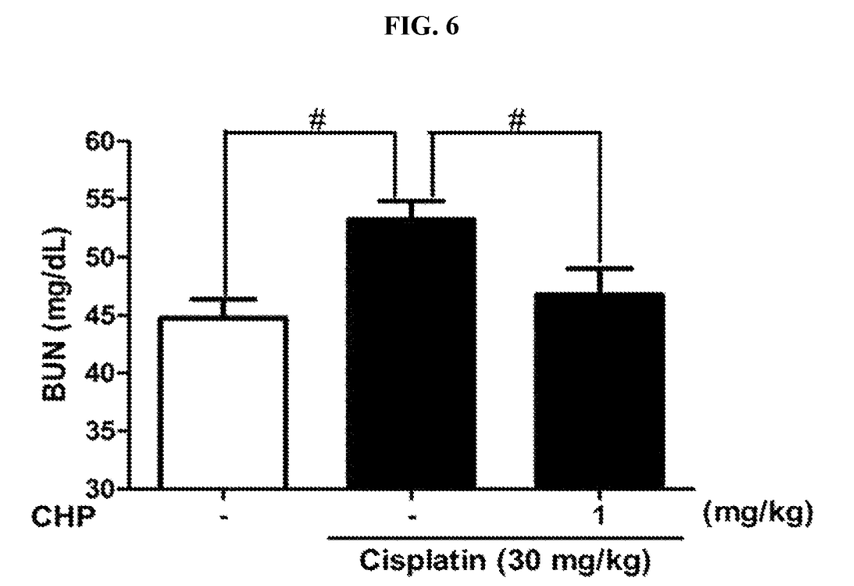
FIG. 6 is a graph of a BUN measurement to confirm that CHP ingestion protects a mouse against kidney toxicity by cisplatin.

The results of the analysis are illustrated in FIG. 6. We performed a t-verification between the liver damage group treated with cisplatin and other experimental groups and verified the significance thereof. These groups showed a statistically significant difference (*p<0.05).

The administration of cisplatin to mice could also lead to kidney damage and increase in BUN. Further, it was confirmed that the cisplatin-induced BUN was significantly reduced in mice that ingested the cyclo histidine-proline (CHP) (FIG. 6).

Thus, the cyclo histidine-proline (CHP) has the effect of reducing the concentration of BUN (blood urea nitrogen), which allows the kidney function value in blood to be measured. Therefore, the pharmaceutical composition including the cyclo histidine-proline (CHP) as the active ingredient is excellent in protecting the kidney cell. Thus, it is also known that such a composition may be usefully used for the prevention or treatment of diseases including the kidney disease. The CHP according to the present disclosure was found to have an excellent effect of inhibiting and reducing the liver and kidney damage induced by the anticancer drug cisplatin. Accordingly, the CHP-including composition may be usefully used as a pharmaceutical composition or health functional food for preventing and treating the liver and kidney toxicity-related diseases induced by the anticancer agent.

The present disclosure has focused on the preferred embodiments. However, those of ordinary skill in the art to which the present disclosure belongs may understand that the present disclosure may be embodied in a modified form without departing from the essential characteristics of the present disclosure. Therefore, the disclosed embodiments should be considered in an illustrative rather than a restrictive sense. The scope of the present disclosure is set forth in the appended claims rather than the foregoing description. All differences within the scope of the claims should be construed as being included in the present disclosure.

What is claimed is:

1. A method of treating a subject suffering from a kidney disease or kidney damage,
    said method comprising administering an effective amount of a composition to the subject,
    wherein the composition comprises cyclo-histidine-proline (CHP) or a pharmaceutically acceptable salt thereof, as an active ingredient, and
    wherein the kidney disease or kidney damage excludes acute renal failure.

2. The method of claim 1, wherein the administering the composition:
    (a) lowers a blood urea nitrogen level in the subject; and/or
    (b) lowers a blood creatinine level in the subject; and/or
    (c) inhibits kidney cell apoptosis in the subject.

3. The method of claim 1, wherein the composition further comprises one or more additives selected from the group consisting of sodium starch glycolate, crospovidone, croscarmellose sodium, alginic acid, carboxymethylcellulose calcium, carboxymethylcellulose sodium, chitosan, guar gum, low-substituted hydroxypropylcellulose, magnesium aluminum silicate, polacrilin potassium, starch, gelatinized starch, microcrystalline cellulose, povidone, colloidal silicon dioxide, calcium hydrogen phosphate, lactose, mannitol, sugar, arabic gum, pregelatinized starch, corn starch, powdered cellulose, hydroxypropylcellulose, opadry, sodium starch glycolate, carnauba lead, synthetic aluminum silicate, stearic acid, magnesium stearate, aluminum stearate, calcium stearate, white sugar, dextrose, sorbitol, and talc.

4. The method of claim 2, wherein the kidney disease or kidney damage is chronic and accompanied with kidney cell apoptosis.

5. The method of claim 1, wherein the kidney disease or kidney damage is caused by administration of a drug.

6. The method of claim 5, wherein the drug is a platinum-based anticancer drug or an antibiotic agent.

7. The method of claim 6, wherein the drug is cisplatin, carboplatin, oxaliplatin, or nedaplatin.

8. The method of claim 6, wherein the antibiotic agent is gentamycin (GM) or acetaminophen (APAP).

9. The method of claim 1, wherein the composition is an oral composition.

10. The method of claim 1, wherein the kidney disease is chronic kidney disease.

11. The method of claim 3, wherein the kidney disease is chronic kidney disease.

12. A method of inhibiting kidney cell apoptosis in a subject with kidney disease or kidney damage, comprising administering a composition to the subject in an amount effective to inhibit kidney cell apoptosis,
   wherein the composition comprises
   (a) cyclo histidine-proline (CHP) or its pharmaceutically acceptable salt, as an active ingredient, and
   (b) one or more additives selected from the group consisting of sodium starch glycolate, crospovidone, croscarmellose sodium, alginic acid, carboxymethylcellulose calcium, carboxymethylcellulose sodium, chitosan, guar gum, low-substituted hydroxypropylcellulose, magnesium aluminum silicate, polacrilin potassium, starch, gelatinized starch, microcrystalline cellulose, povidone, colloidal silicon dioxide, calcium hydrogen phosphate, lactose, mannitol, sugar, arabic gum, pregelatinized starch, corn starch, powdered cellulose, hydroxypropylcellulose, opadry, sodium starch glycolate, carnauba lead, synthetic aluminum silicate, stearic acid, magnesium stearate, aluminum stearate, calcium stearate, white sugar, dextrose, sorbitol, and talc, to the subject, and
   wherein the kidney disease or kidney damage is chronic.

13. The method of claim 12, wherein the administering the composition to the subject reduces a blood urea nitrogen level and/or creatinine level in the subject.

14. The method of claim 12, wherein the composition is an oral composition.

* * * * *